US008691752B2

(12) United States Patent
Sarrias Fornés et al.

(10) Patent No.: US 8,691,752 B2
(45) Date of Patent: Apr. 8, 2014

(54) PROTEIN PRODUCT FOR TREATMENT OF INFECTIOUS DISEASES AND RELATED INFLAMMATORY PROCESSES

(75) Inventors: Maria Rosa Sarrias Fornés, Barcelona (ES); Francisco Lozano Soto, Barcelona (ES)

(73) Assignee: Universidad de Barcelona, Barcelona (ES)

(*) Notice: Subject to any disclaimer, the term of this patent is extended or adjusted under 35 U.S.C. 154(b) by 1063 days.

(21) Appl. No.: 12/593,140

(22) PCT Filed: Mar. 27, 2008

(86) PCT No.: PCT/ES2008/000177
§ 371 (c)(1),
(2), (4) Date: Sep. 25, 2009

(87) PCT Pub. No.: WO2008/119851
PCT Pub. Date: Oct. 9, 2008

(65) Prior Publication Data
US 2010/0105622 A1 Apr. 29, 2010

(30) Foreign Application Priority Data
Mar. 28, 2007 (ES) .................................. 200700893

(51) Int. Cl.
*A61K 38/00* (2006.01)
*A61K 39/38* (2006.01)
*A61P 31/10* (2006.01)
*A61P 5/00* (2006.01)
*A01N 37/18* (2006.01)

(52) U.S. Cl.
USPC ............ 514/1.4; 514/1.1; 514/3.4; 424/184.1

(58) Field of Classification Search
None
See application file for complete search history.

(56) References Cited

U.S. PATENT DOCUMENTS

| 6,315,999 | B1 | 11/2001 | Sadoff et al. |
| 6,534,648 | B1 | 3/2003 | Pardy et al. |
| 8,404,633 | B2* | 3/2013 | Lozano Soto et al. ......... 514/1.1 |
| 2002/0002178 | A1 | 1/2002 | Misra |
| 2002/0006915 | A1 | 1/2002 | Strong et al. |
| 2002/0044929 | A1 | 4/2002 | Fisher et al. |
| 2002/0155094 | A1 | 10/2002 | White et al. |
| 2002/0165138 | A1 | 11/2002 | Ward et al. |
| 2003/0008822 | A1 | 1/2003 | Dinarello et al. |
| 2003/0021783 | A1 | 1/2003 | Kitajima et al. |
| 2003/0114377 | A1 | 6/2003 | Kirkland et al. |
| 2010/0105622 | A1* | 4/2010 | Sarrias Fornes et al. ....... 514/12 |
| 2011/0195894 | A1* | 8/2011 | Lozano Soto et al. ......... 514/3.4 |

FOREIGN PATENT DOCUMENTS

| EP | 2143436 | * | 1/2010 |
| WO | 93/19772 | A1 | 10/1993 |
| WO | 95/12614 | | 5/1995 |
| WO | WO 2005/016962 | A2 * | 2/2005 |
| WO | 2006/056492 | A1 | 6/2006 |
| WO | WO 2008/119851 | A1 * | 10/2008 |
| WO | WO 2009/153336 | A1 * | 12/2009 |

OTHER PUBLICATIONS

Adler, Elizabeth M. CS Science's STKE, AAAS, Washington, DC 20005, USA ,SO Signal Transduction Knowledge Environment [Signal Transduct. Knowl. Environ.], (20070700) vol. 2007, No. 395, pp. tw252-tw252. (abstract only).*
Sarrias et al, 11724-11729 PNAS Jul. 10, 2007 vol. 104 No. 28.*
Vera et al, 1506-1511 PNAS Feb. 3, 2009 vol. 106 No. 5.*
Aruffo et al, J. Exp. Med., Oct. 1991, 174:949-952.*
Whitney et al, J. Biol. Chem., Aug. 4, 1995, 270/31:18187-18190.*
Sarrias M.R. et al. CD6 binds to pathogen-associated molecular patterns and protects from LPS—induced septic shock. Proceedings of the National Academy of Sciences. Oct. 7, 2007, vol. 104, No. 28, pp. 11724-11729.
Stelter F. et al. Different efficacy of soluble CD14 treatment in high- and low-dose LPS model. European Journal of Clinical Investigation. 1998, vol. 28, No. 3, pp. 205-213.
Severe sepsis and septic shock: review of the literature and emergency department management guidelines, H.B. Nguyen et al., Ann. Emergency Med. 2006, vol. 48, pp. 28-54.
M.R. Sarrias et al., "The Scavenger Receptor Cysteine-Rich (SRCR) domain: an ancient and highly conserved protein module of the innate immune system", Crit. Rev. Immunol. 2004, vol. 24, pp. 1-37.
M.A. Bowen et al., "Adhesion Molecules, Their Receptors, and Their Regulation: Analysis of CD6-Activated Leukocyte Cell Adhesion Molecule (ALCAM/CD166) Interactions", Transplantation Proceedins, 31, 795-796, 1999 by Elsevier Science Inc.
M. Simarro et al., "The cytoplasmic domain of CD5 mediates both TCR/CD3-dependent and -independent diacylglycerol production", J. Immunol. 1997, vol. 159, pp. 4307-4315.
I. Gimferrer et al., "The accessory molecules CD5 and CD6 associate on the membrane of lymphoid T cells", J. Biol. Chem. 2003, vol. 278, pp. 8564-8571.

(Continued)

Primary Examiner — Nita M Minnifield
(74) Attorney, Agent, or Firm — Roberts Mlotkowski Safran & Cole, P.C.

(57) ABSTRACT

The inventors have found that CD6, a member of the Scavenger Receptor Cysteine-Rich (SRSR) superfamily expressed on human lymphocytes binds to Gram-positive and Gram-negative bacteria, as well as to other microbial structures. Thus, a CD6 product is useful for the manufacture of a medicament for therapeutic and/or preventive treatment of an infectious disease or of an inflammatory condition related to an infectious disease or to the presence of a product derived from an infectious agent in a mammal including a human. Examples of such inflammatory conditions are systemic inflammatory response syndrome (SIRS), sepsis, severe sepsis and septic shock.

9 Claims, 9 Drawing Sheets

(56) References Cited

OTHER PUBLICATIONS

L. Cardenas et al., "Phosphorylation-Dephosphorylation of the CD6 Glycoprotein Renders 2 Isoforms of 130 and 105 Kilodaltons—Effect of Serum and Protein-Kinase-C Activators" Journal of Immunology 1990, vol. 145, pp. 1450-1455.

E. Kohfeldt et al., "Properties of the extracellular calcium binding module of the proteoglycan testican", 1997, FEBS Lett. vol. 414, pp. 557-561.

M.R. Sarrias et al., "A role for human SP alpha as a pattern recognition receptor", J. Biol. Chem. 2005, vol. 280, pp. 35391-35398.

M. Ramos-Casals et al., "High circulating levels of soluble scavenger receptors (sCD5 and sCD6) in patients with primary Sjogren's syndrome" Rheumatology 2001, vol. 40, pp. 1056-1059.

R.R. Skelly et al., "Stimulation of T-independent antibody responses by hapten-lipopolysaccharides without repeating polymeric structure", Infect. Immun. 1979, vol. 23, pp. 287-293.

P.S. Tobias et al., "Lipopolysaccharide binding protein-mediated complexation of lipopolysaccharide with soluble CD14", J. Biol. Chem. 1995, vol. 270, pp. 10482-10488.

I. Garcia-Verdugo et al. "Interaction of SP-A (surfactant protein A) with bacterial rough lipopolysaccharide (Re-LPS), and effects of SP-A on the binding of Re-LPS to CD14 and LPS-binding protein", Biochemical Journal 2005, vol. 391, pp. 115-124.

Calvo et al., "Identification of a natural soluble form of human CD5" Tissue Antigens 1999, vol. 54, pp. 128-137.

D.W. Dunne et al., "The Type-I Macrophage Scavenger Receptor Binds to Gram-Positive Bacteria and Recognizes Lipoteichoic Acid", Proceedings of the National Academy of Sciences of the United States of America 1994, vol. 91, pp. 1863-1867.

W.H. Robinson et al., "Human CD6 possesses a large, alternatively spliced cytoplasmic domain", Eur. J. Immunol. 1995, vol. 25, pp. 276.

International Search Report PCT/ES2008/000177 mailed Aug. 18, 2008.

Ayyagoo, V. et al. "HIV-1 viral protein (Vpr) regulates viral replication and cellular proliferation in T cells and monocytoid cells in vitro" Journal of Leukocyte Biology, vol. 62, Jul. 1997, pp. 93-99.

Oldstone, M. "How viruses Escape from Cytoxic T Lymphocytes: Molecular Parameters and Players"Virology, vol. 234, 1997, pp. 179-185.

Hawiger, J. "Innate Immunity and Inflammation: A Transcriptional Paradigm" Immunologic Research, vol. 23, No. 2-3, 2001, pp. 99-109.

Bott, C. et al. "Transcriptional Regulation of CD6 Expression on Human T Lymphocytes by Phorbol Ester" The Journal of Immunolgy, 1994, vol. 153, No. 1, pp. 1-9.

Robinson W. et al. "Human CD6 possesses a large, alternatively spliced cytoplasmic domain" Eur J. Immunol, 1995, 25, pp. 2765-2769.

J. Biol. Chem. 1996, 271 No. 29: 17390-17396, Bowen et al. "The Amino-terminal Immunoglobulin-like Domain of Activated Leukocyte Cell Adhesion Molecule Binds Specifically to the Membrane-proximal Scavenger Receptor Cysteine-rich Domain of CD6 with a 1:1 Sotichiometry".

Stelter F. et al.: ,, Different efficacy of soluble CD14 treatment in high- and low-dose LPS model, European Journal of Clinicla Investigation, vol. 28, No. 3, 1998, pp. 205-213.

Ibanez A. et al.: "Mitogen-activated protein kinase pathway activation by the CD6 lymphocyte surface receptor", The Journal of Immunology, vol. 177, Jul. 2006, pp. 1152-1159.

European Search Report 08750412.2-1456/2143436 PCT/ES2008000177 dated Oct. 23, 2013177, Jul. 2006, pp. 1152-1159.

* cited by examiner

A

B

A  Coomassie
B  WB: Sav-HRP
C  WB: PoAb α-CD6

D

PROTEIN PRODUCT FOR TREATMENT OF INFECTIOUS DISEASES AND RELATED INFLAMMATORY PROCESSES

CROSS-REFERENCE TO RELATED APPLICATIONS

The present Application is a US national phase of PCT/ES2008/000177 filed on Mar. 27, 2008 ("PCT Application"), which claims priority from Spanish Application No. P200700893 filed on Mar. 28, 2007, both of which are hereby incorporated by reference in their entirety into the present Application.

This invention relates to the field of medicine, and specifically to compounds of protein nature for the manufacture of medicaments for therapeutic and/or preventive treatment of infectious diseases and of inflammatory conditions related thereto.

BACKGROUND ART

Systemic microbial infection and release of microbial products induces the hyperactivation of host immune cells, subsequently generating an exacerbated inflammatory response. Sepsis may result in the inability of the immune system to control this inflammation, and can end in tissue injury, increased vascular permeability and it can cause multi-organ failure and shock (septic shock).

Sepsis can result from many causes but is typically triggered by pneumonia, trauma, surgery, and burns or by conditions such as cancer or AIDS. Sepsis usually begins with tremor, fever, falling blood pressure (septic shock), rapid breathing, rapid heart rate, and skin lesions. Within hours, sepsis may cause spontaneous clotting in blood vessels, severe hypotension, multiple organ failure, shock, gangrene and eventually death. Sepsis causes high morbidity and mortality in humans and other animals (mortality of up to 70% in septic patients). In the United States and Europe, 1.5 million people develop sepsis annually. 30% of these patients die after one month and a 20% after six months. In the United States, sepsis is the $10^{th}$ cause of death, which represents a mortality higher than those caused by infarct, breast cancer or lung cancer.

The most important intervention in sepsis is quick diagnosis and treatment. Diagnosing sepsis can be difficult. Some of its symptoms, such as fever, rapid pulse, and respiratory difficulty occur frequently and can be confused as being due to other disorders. Patients diagnosed with severe sepsis are usually placed in the intensive care unit (ICU) of the hospital for special treatment. The first line of treatment is to identify and eliminate the underlying infection with anti-infection agents or surgery to drain the site of infection. Current methods for treating sepsis include antibacterials, antibodies, peptides, and a recombinant human activated protein C named drotecogin alpha, marketed by Eli Lilly as Xigris®. However, drotecogin alpha only reduces the mortality associated with severe sepsis in a 5%, and not all the patients respond positively to this drug. Steroids have also been recently shown to be valuable in patients with septic shock. The doctor also administers intravenous fluids to prevent blood pressure from dropping too much. In some cases, vasopressor medications (which constrict blood vessels) are needed to achieve an adequate blood pressure. Finally, if organ failures occur, appropriate supportive care is provided (e.g., dialysis for kidney failure, mechanical ventilation for respiratory failure, etc.).

Due to the high level of redundancy regarding molecular mediators in the sepsis response, new approaches are likely to focus on intervening at multiple points in the sepsis cascade. Some drug candidates in early phase of development are a Triggering Receptor Expressed on Myeloid cells-1 (TREM-1) receptor antagonist (Merck & Co Inc and BioXell SpA); a super-antigen antagonist (Atox Bio Ltd.), a short peptide which blocks the action of a family of deadly bacterial toxins produced by *Staphylococcus aureus* and *Streptococcus pyogenes*, termed as super-antigens; Immune Regulating Hormone (IRH, Hollis-Eden Pharmaceuticals Inc.), an autoimmune and anti-inflammatory drug which controls immune system and metabolic functions; and an Adenosine A1 receptor antagonist as a treatment for Gram-negative septicemia (Endacea Inc.). Other molecules under development are Toll-like Receptor-4 antagonists (Takeda and Eisai); anti-TNF-alfa polyclonal antibody fragment (Protherics); bovine intestine-derived alkaline phosphatase (AM-Pharma); Norathiol (Medinox), which neutralizes nitric oxide; and transgenic antithrombin III ATryn® (GTC Biotherapeutics) which received marketing approval from European regulatory authorities in 2006 and it is in late-stage clinical trials in the United States.

Other approaches have been proposed for treating sepsis, such as: anti-IL-8 antibodies (US Patent Publication No. 20030021783A), anti-IL-18 antibodies (US 20030008822A), anti-C5a antibodies and C-terminal truncated C5a peptides (US 20020165138A), chemokines and chemokine fragments (US 20020155094A), a combination of protein C and BPI antibodies (US 20020044929A), COX-2 inhibitors (US 20020006915A), algae lipopolysaccharides (U.S. Pat. No. 6,534,648) and using an antibody to TNF-α and an antibody to bacterial lipopolysaccharide (U.S. Pat. No. 6,315,999). However, despite the major advances of the past several decades in the treatment of serious infections, the incidence of sepsis and mortality due to sepsis continue to increase. Therefore, it seems desirable to provide new methods and compositions for the prevention and treatment of infectious diseases and of inflammatory conditions related to these infectious diseases.

SUMMARY OF THE INVENTION

Inventors have found that the ectodomain of human CD6, a cell surface receptor mainly expressed by cells of the lymphoid lineage, is able to bind to conserved microbial structures such as lipopolysaccharide (LPS) and lipotheicoic acid (LTA) from Gram-negative and Gram-positive bacteria, respectively. Surprisingly, the LPS-CD6 interaction show a relative high affinity similar in magnitude to that reported for the interaction of LPS with CD14, the most important LPS receptor in mammalian cells. CD6 binds to Re-LPS about 10-fold more tightly than Spα, another receptor with Scavenger Receptor Cysteine-Rich (SRCR) domains. These data lead to the finding that i.p. administration of a recombinant form of CD6 abolishes the lethal effects caused by LPS-induced septic shock in mice. Accordingly, CD6 has therapeutic potential for the intervention of septic shock syndrome and of other inflammatory diseases related to infectious diseases.

Innate immune responses rely on the ability of multiple non-polymorphic germline-encoded receptors to recognize the so-called Pathogen-Associated Molecular Patterns (PAMPs), which are conserved products of microbial pathogens, not shared by the host, and essential for their survival. Pattern-Recognition Receptors (PRRs) are mainly expressed by phagocytic cells (granulocytes, macrophages, dendritic cells) and cells of epithelial barriers. Some of them have been shown to directly interact with a variety of microbial components. Herein the inventors have surprisingly found that CD6, a member of the SRCR superfamily expressed on human lymphocytes, binds to Gram-positive and Gram-negative bacteria, as well as to other microbial (viral, fungal) structures. The main reported role of CD6 is the modulation of T cell activation and differentiation signals. It is surprising that in addition, CD6 has the ability of sensing the presence of microbial components. This is a surprising activity of lymphocytes, since this activity has been related to macrophages, which express receptors such as CD14 and Spa. Interestingly, competition binding experiments show that the interaction of CD6 with the bacterial surfaces is specific. In contrast to CD6, the recombinant form encompassing the ectodomain of CD5 do not bind to bacteria or to LPS. Data also show that CD6 binds to LTA and LPS through independent and non-overlapping sites of the molecule.

Presence of CD6 induces bacterial aggregation. The bacterial aggregation data, together with the aggregation of LPS induced by CD6 in the presence of $Ca^{2+}$, indicate that CD6 may contribute to increase the size of invading bacteria as well as of LPS particles. This would facilitate particle clearance from the circulation, and reduce subsequent inflammatory processes, which in cases such as sepsis may even result fatal. Accordingly, administration of a single dose (25 μg) of CD6 into mice one hour prior to LPS challenge significantly enhanced their survival rate (up to 70%) as compared to CD5 or saline treatment, and concomitantly induced a significant reduction on the serum levels of pro-inflammatory cytokines TNF-α, IL-1β and IL-6 in these mice.

Low levels of soluble CD6 have been detected in normal human sera by ELISA assays, but its biochemical characterization has not been achieved until present. By using affinity chromatography techniques, a natural soluble CD6 (nsCD6) protein has been purified from pooled human sera with similar molecular weight (MW), antibody reactivity and cell binding characteristics than the recombinant form of CD6, and exclusively composed of the ectodomain of human CD6. These data, together with the shared ability to bind to LPS in ELISA assays, indicate that CD6 retains the biological activity of the circulating form of CD6 and validate the use of recombinant CD6 in the studies given the low availability of natural CD6 (it is present in serum at concentrations around 5.27 ng/ml). These results also validate the potential use of a recombinant form of CD6 to be administered to a patient.

Accordingly, the present invention relates to the use of a CD6 product for the manufacture of a medicament for therapeutic and/or preventive treatment, in a mammal including a human, of an infectious disease, or of an inflammatory condition related to an infectious disease, or of an inflammatory disease related to the presence of a product derived from an infectious agent.

The invention may alternatively be formulated as a method for therapeutic and/or preventive treatment in a mammal including a human, of an infectious disease, or of an inflammatory condition related to an infectious disease, or of an inflammatory disease related to the presence of a product derived from an infectious agent, comprising administering to said mammal in need thereof an effective amount of CD6 product.

In a particular embodiment of the invention, the infectious disease is a microbial infection. In more particular embodiments, the microbial infection is selected from the group consisting of a bacterial infection (either Gram-negative or Gram-positive bacteria), a parasitic infection, a viral infection, a fungal infection and combinations thereof (polymicrobial infection).

In another particular embodiment, the infectious disease is a septicemia. As used herein, the term "septicemia" refers to the presence of any microbe in blood stream. Particularly, the septicemia is selected from the group consisting of a bacteremia, a viremia, a fungemia, a parasitemia and combinations thereof.

The presence of viable microbes is found in most cases of inflammatory conditions related to an infectious disease, whereas 20% to 30% of patients do not have microbes identified from any source but products derived from them. Thus, in another embodiment, the inflammatory condition is related to a product derived from an infectious agent. Particularly, the infectious agent is selected from the group consisting of a bacterium, a parasite, a virus, a fungus, and combinations thereof.

Sepsis is defined as the presence or presumed presence of an infection accompanied by evidence of a systemic response called the systemic inflammatory response syndrome (SIRS). For sepsis definition, reference is made to the article "Severe sepsis and septic shock: review of the literature and emergency department management guidelines", H. B. Nguyen et al., *Ann. Emergency Med.* 2006, vol. 48, pp. 28-54. Sepsis is usually caused by bacterial infections (either Gram-negative or Gram-positive bacteria) but can also be caused by other pathogens. Most often however, sepsis is caused by Gram-negative bacteria infections. In this case, however, the injury and symptoms attributable to sepsis are not only caused by the bacteria but are also caused by a component of the bacteria cell wall known as endotoxin or LPS. LPS molecules are glycolipids that are ubiquitous in the outer membrane of Gram-negative bacteria. LPS is released when the immune system destroys the invading bacteria. The released LPS binds to monocytes, macrophages, and endothelial cells and triggers the production of various mediators such as TNF-α and interleukins (IL-1, IL-6, and IL-8). Production of excessive TNF-α, IL-1, IL-6, and IL-8 is a major cause of severe forms of sepsis.

In a particular embodiment of the invention, the inflammatory condition is SIRS. In another particular embodiment, the inflammatory condition is sepsis. SIRS is defined as the presence of two or more of the following: (1) temperature greater than 38° C. or less than 36° C.; (2) pulse rate greater than 90 beats/min; (3) respiratory rate greater than 20 breaths/min (or $PCO_2$ less than 32 torr); and (4) white blood cells count greater than $12000/mm^3$ or less than $4000/mm^3$, or greater than 10% immature band forms.

In another particular embodiment, the inflammatory condition is severe sepsis. Severe sepsis is defined as the sepsis which is accompanied by one or more organ dysfunctions. Organ dysfunction can be defined as acute lung injury; coagulation abnormalities; thrombocytopenia; altered mental status; renal, liver, or cardiac failure; or hypoperfusion with lactic acidosis.

Finally, in another particular embodiment, the inflammatory condition is septic shock. Septic shock is defined as the presence of sepsis and refractory hypotension, i.e., systolic blood pressure less than 90 mmHg, mean arterial pressure less than 65 mmHg, or a decrease of 40 mmHg in systolic blood pressure compared to baseline unresponsive to a crystalloid fluid challenge of 20 to 40 ml/kg. Thus, septic shock is effectively a form of severe sepsis.

The source of the infection can be any of a number of places throughout the body. Common sites of infection that can lead to sepsis comprise the following:

inflammation of the appendix (appendicitis), diverticulitis, bowel problems, infection of the abdominal cavity (peritonitis), and gallbladder or liver infections;

inflammation or infections of the brain or the spinal cord;

lung infections such as pneumonia;

skin infections through wounds or through openings made with intravenous catheters, cellulitis (inflammation of the skin's connective tissue);

urinary tract infections, especially if the patient has a urinary catheter to drain urine;

dental and gynecological examinations or treatments;

blunt or penetrating trauma, surgery, and endocarditis.

Definition of CD6 Product

The CD6 receptor is a lymphoid-specific surface glycoprotein expressed on the membrane of thymocytes, mature T cells, and the B1a B cell subset, although CD6 expression has also been reported on certain regions of the brain. The CD6 receptor belongs to the SRCR superfamily characterized by the presence of one or several repeats of a cysteine-rich extracellular domain named SRCR (cf. M. R. Sarrias et al., "The Scavenger Receptor Cysteine-Rich (SRCR) domain: an ancient and highly conserved protein module of the innate immune system", Crit. Rev. Immunol. 2004, vol. 24, pp. 1-37). Its extracellular region is exclusively composed of three consecutive SRCR domains. Functionally, it is physically associated to the antigen-specific receptor complex present on T (TCR/CD3) and B (BCR) cells, where CD6 contributes to either positive or negative modulation of the activation and differentiation signals delivered by that receptor complex. It is well accepted that CD6 binds to its natural ligand ALCAM ("Activated Leukocyte Cell Adhesion Molecule", also known as CD166) cf., Bowen et al., "Adhesion Molecules, Their Receptors, and Their Regulation: Analysis of CD6-Activated Leukocyte Cell Adhesion Molecule (AL-CAM/CD166) Interactions", Transplantation Proceedings, 31, 795-796, 1999), a broadly expressed adhesion molecule of the Ig superfamily.

As used herein, the term "CD6 product" means a product comprising the CD6 ectodomain or a fragment thereof. Ectodomain refers to the three SRCR domains with the intervening sequences and the stalk region which separates it from the membrane. Suitable CD6 products include natural, synthetic, or recombinant biologically active polypeptide of CD6 ectodomain or fragments thereof; biologically active polypeptide variants of CD6 ectodomain or fragments thereof, including hybrid fusion proteins or dimers; or to biologically active polypeptide analogs of CD6 ectodomain or fragments thereof. Analogs include products where one or more amino acid residues have been replaced by a different amino acid. Conservative amino acid substitutions are preferred.

CD6 product is from mammalian origin and more preferably from human origin.

Human CD6 is 100 to 130 kDa. The human full length CD6 protein described in GenBank Accession number NP_006716 has 668 amino acids. The ectodomain is composed of three SRCR domains, the intervening sequences and a stalk region.

In a particular embodiment, the CD6 product of the invention comprises the amino acid sequence SEQ ID NO: 1. This sequence includes the three SRCR domains, the intervening sequences and the stalk region. In another embodiment, the CD6 product is a murine CD6 product.

Due to the low plasma levels of CD6, it is not industrially viable to obtain CD6 from purification plasma or serum. Thus, for the purpose of the invention, it is preferred to produce the CD6 product by genetic engineering methods. Any method commonly used in the art can be employed to produce recombinant CD6, hereafter referred as rCD6. A preferred method to express and purify rCD6 is described below in the examples. This method allows to produce rCD6 for experimental purposes, so industrial scaling-up is necessary to produce large amounts of rCD6. The CD6 of the present invention may also be expressed as a fusion protein.

To test whether a CD6 product is suitable for the purpose of the invention, a microbial binding assay may be used. A suitable assay is described in Example 1.

According to the teaching of the present invention, the CD6 product can be administrated to a mammalian, preferably a human. The purpose of the administration of the CD6 product may be preventive (to avoid the development of these diseases) and/or therapeutic (to treat these diseases once they have been developed/installed).

It is to be understood that the CD6 product is administered in a pharmaceutically acceptable form. Those skilled in the art may ascertain the proper dose using standard procedures. It is understood that the dose should be an effective amount of CD6 product in the sense that a reduced inflammatory response is seen in the treated subject.

The CD6 product of the invention can be administered alone or in a composition with pharmaceutically acceptable carriers or excipients. The skilled in the art will adapt the composition depending on the particular mode of administration. The compositions may comprise the CD6 product as a single agent against the infectious diseases or the inflammatory conditions related thereto, combinations of such agents, or combinations with other therapeutic agents depending on the condition.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention.

In the examples and drawings, rsCD6 refers to the recombinantly soluble obtained CD6 ectodomain to be distinguished from the CD6 receptor bound to membrane.

DETAILED DESCRIPTION OF PARTICULAR EMBODIMENTS

Cells

Figure 1:
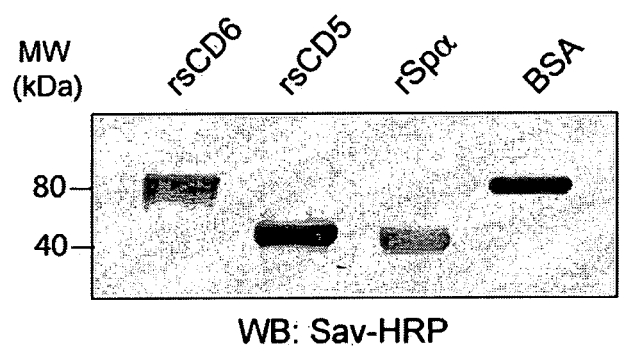
FIG. 1 shows binding of rsCD6 to Gram-positive and Gram-negative bacteria. A) Western blot analysis of the affinity-purified biotin-labeled proteins with streptavidin-HRP. B) Binding of biotinylated proteins (BSA, rsCD5, rSpα and rsCD6) to E. coli and S. aureus. C) Calcium-dependence of the binding of biotin-labeled rsCD6 and rSpα to E. coli and S. aureus. TPA means "total protein added". D) Competition binding assays of rsCD6-biotin to E. coli and S. aureus in the presence of increasing concentrations of LPS or LTA. C means "competitor".
Figure 1:
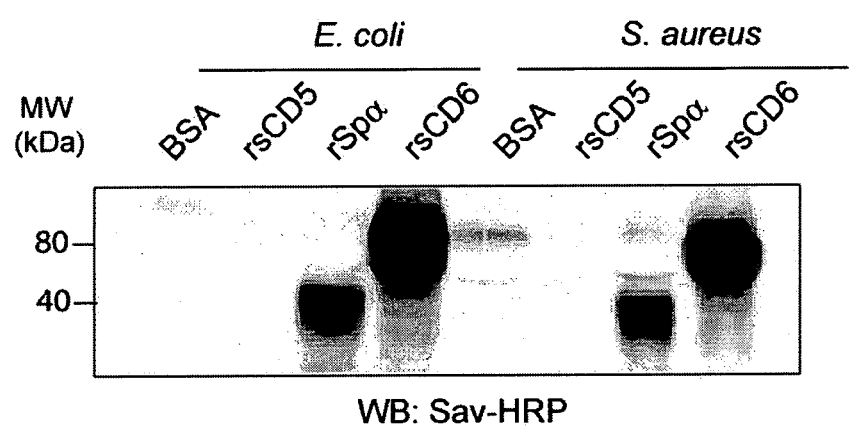
Figure 1:
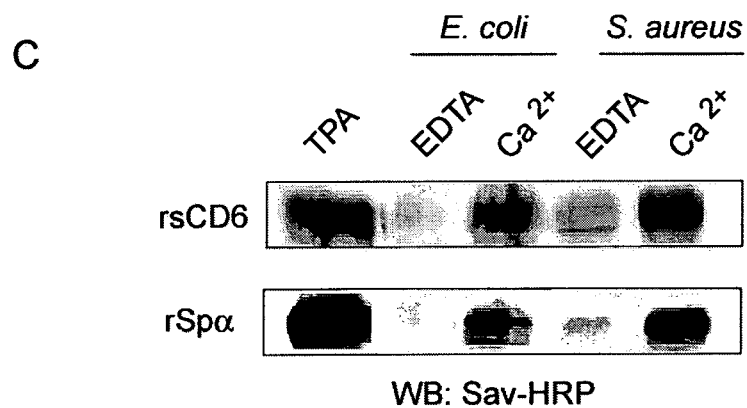
Figure 1:
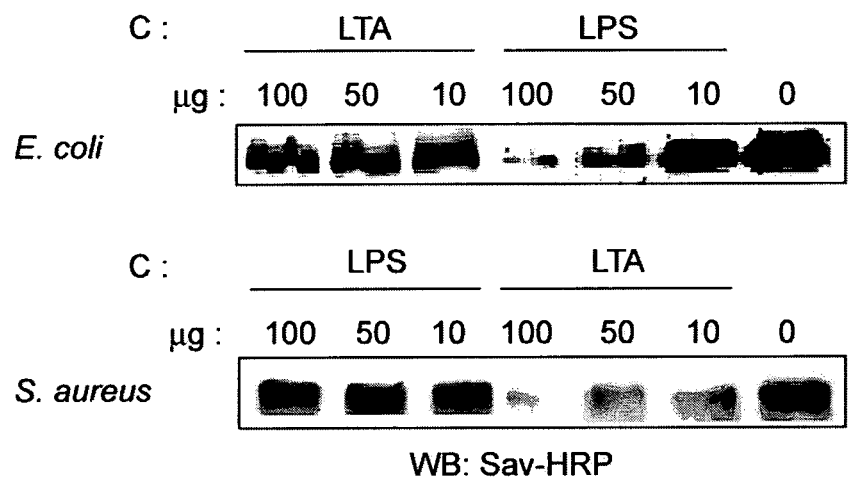

The human lymphoblastoid B cell line Raji, the erythromyeloid cell line K562, as well as the leukemic T cell line HUT-78, were obtained from the American Type Culture Collection (ATCC, Manassas, Va.). The CD5- and CD6-negative Jurkat 2G5 cells were obtained by Fluorescent Activated Cell Sorting (FACS) and further cloning of Jurkat cells, as reported (M. Simarro et al., "The cytoplasmic domain of CD5 mediates both TCR/CD3-dependent and -independent diacylglycerol production", *J. Immunol.* 1997, vol. 159, pp. 4307-4315). The 2G5 Jurkat cells were stably transfected with the $pH^\beta$-CD6.wt construct. Briefly, the expression construct coding for wild-type CD6 ($pH^\beta$-CD6.wt) was obtained by cloning SalI/EcoRI- and EcoRI/BamHI-restricted (Fermentas MBI) fragments corresponding to the extracellular and cytoplasmic regions of CD6, respectively, into SalI/BamHI-restricted $pH^\beta$APr-1-neo mammalian expression vector. The extracellular portion of CD6 was obtained by PCR amplification using the 5'TCTCGTCGACATGTG-GCTCTTCTTCGGGAT3' (SEQ ID NO: 2) and 5'AACT-TCTTTGGGGATGGTGATGGG3' (SEQ ID NO: 3) primers and the CD6-PB1 cDNA sequence cloned into pBJneo as a template. The intracellular region of CD6 was obtained by PCR amplification of HUT78 cDNA with the 5'GTCAC-TATAGAATCTTCTGTG3' (SEQ ID NO: 4) and 5'AAAG-GATCCCTAGGCTGCGCTGATGTCATC3' (SEQ ID NO: 5) primers (cf. I. Gimferrer et al., "The accessory molecules CD5 and CD6 associate on the membrane of lymphoid T cells", *J. Biol. Chem.* 2003, vol. 278, pp. 8564-71).

Unless indicated, all cells used in this study were grown in RPMI 1640 medium (Life Technologies, Gaithesburg, Md.) supplemented with 100 U/ml penicillin, 100 μg/ml streptomycin and 10% FCS (GIBCO Invitrogen, Paisley, UK). The human embryonic kidney epithelial cell line HEK 293-EBNA (Invitrogen Life Technologies, Paisley, U.K.) was grown in Dulbecco's modified Eagle's medium (DMEM/F12; Invitrogen Life Technologies), supplemented with 100 U/ml penicillin, 100 μg/ml streptomycin, 250 μg/ml geneticin (G418), and 10% FCS.

Antibodies and Reagents

The mAbs Cris-1 (anti-CD5, IgG2a) and 161.8 (anti-CD6, IgG1) were produced by Dr. R. Vilella (Hospital Clinic, Barcelona, Spain). The mouse anti-human CD6 mAbs MAE1-C10 (IgG1) and SPV-L14.2 (IgG1) were provided by Drs. F. Sánchez-Madrid (Hospital de la Princesa, Madrid, Spain) (cf. L. Cardenas et al., "Phosphorylation-Dephosphorylation of the CD6 Glycoprotein Renders 2 Isoforms of 130 and 105 Kilodaltons—Effect of Serum and Protein-Kinase-C Activators" *Journal of Immunology* 1990, vol. 145, pp. 1450-55) and Jo Hilders (Bioprobe B.V., The Netherlands), respectively. The rabbit polyclonal antiserum against the extracellular region of human CD6 was produced in the laboratory by immunization with rsCD6 (cf. I. Gimferrer et al., *J. Biol. Chem.* 2003, vol. 278, pp. 8564-71).

The following reagents were purchased: HRP-conjugated streptavidin (DakoCytomation, Glostrop, Denmark); FITC-conjugated rabbit anti-mouse Ig (Sigma-Aldrich, St. Louis, Mo., USA); purified LPS from *E. coli* (O55:B5, O26:B6, O111:B4) and Lipoteichoic Acid (LTA) from *S. aureus*, as well as FITC-LPS from *E. coli* O111:B4 (Sigma-Aldrich). PBS (Roche Diagnostics, Indianapolis, USA) is 137 mM NaCl, 3 mM KCl, 8 mM $Na_2HPO_4$, 1.5 mM $KH_2PO_4$, pH 7.4; TBS is 140 mM NaCl, 50 mM Tris-HCl, pH 7.4. HSA was from Grífols (Grífols, Barcelona, Spain). The Re-LPS, a Re595 mutant of LPS from *Salmonella* Minnesota, was from Sigma. Fluorescein, and fluorescein-5-isothiocyanate (FITC, isomer I) were from Molecular Probes (Eugene, Oreg.). Methanol and chloroform used to dissolve Re-LPS were HPLC-grade (Scharlau, Barcelona).

Expression and Affinity-purification of Recombinant Soluble Proteins

The ectodomain of human CD6 (rsCD6 amino acids D25 to E384, immature protein numbering) was expressed using an episomal expression system in human embryonic kidney cells (HEK 293-EBNA). These cells constitutively express the Epstein Barr viral protein EBNA-1, allowing episomal replication of the pCEP-Pu vector, a kind gift from Drs T. Sasaki and R. Timpl (Max Planck Institute for Biochemistry, Martinsried, Germany) (cf. E. Kohfeldt et al., "Properties of the extracellular calcium binding module of the proteoglycan testican", 1997, *FEBS Lett. Vol.* 414, pp. 557-61). The extracellular region of CD6 was PCR amplified by using the 5'CTTCTAGATGACCAGCTCAACACCACCAGCA3' (SEQ ID NO: 6) and 5'GCGGATCCCTA TTCTATAGT-GACTGTCTGAACA3' (SEQ ID NO: 7) and the CD6-PB1 cDNA as a template (cf. W. H. Robinson et al., "Human CD6 possesses a large, alternatively spliced cytoplasmic domain", *Eur. J. Immunol.* 1995, vol. 25, pp. 276). The PCR product was cloned into the pCEP-Pu vector. The resulting constructs were transfected into HEK 293-EBNA cells. Briefly, $10^6$ cells in 10-cm culture dishes were transfected using the calcium-phosphate method with 20 μg of the plasmids. Transfectants were selected with 1 μg/ml puromycin (Sigma, St. Louis, Mo.) in the culture medium. Cell transfectants expressing rsCD6 were grown to confluence in DMEM/FCS, washed twice with phosphate buffered saline (PBS, Roche Diagnostics, Indianapolis, USA) and exchanged to serum-free medium (DMEM/F12), containing 100 U/ml penicillin, 100 μg/ml streptomycin, 250 μg/ml G418, and 1 μg/ml puromycin. The medium was collected every 48-72 h over a period of 15 days. The recombinant protein was affinity-purified over a CNBr-activated Sepharose 4B column covalently coupled to mAb 168.1 (anti-CD6). Unbound protein was then washed off with PBS containing 0.5 M NaCl, and 1% NP40. The protein was eluted with PBS containing 3.5 M $MgCl_2$, and dialyzed to PBS. The purity of the purified protein, was assessed by SDS-PAGE under reducing conditions, and staining with Coomassie blue.

Protein Biotinylation

Protein biotinylation was performed with EZ-Link PEO-maleimide-activated biotin (Pierce, Perbio Science, Cheshire, UK) following the manufacturer's instructions and as before (cf. M. R. Sarrias et al., "A role for human SP alpha as a pattern recognition receptor", *J. Biol. Chem.* 2005, vol. 280, pp. 35391-8). Free biotin was removed by exchanging the samples to PBS over a HiTrap™ desalting column (Amersham Pharmacia Biotech). Monitoring of the biotinylation reactions was performed by Western blotting analysis.

Bacterial Strains And Bacterial Binding Studies

The *E. coli* and *Staphylococcus aureus* bacterial strains used in this study are clinical isolates characterized by the Department of Microbiology of the Hospital Clinic of Barcelona using standard biochemical procedures. Bacteria were grown overnight in Luria Bertoni broth (LB) at 37° C. with aeration and then harvested by centrifugation at 3500×g for 10 min. Bacterial pellets were re-suspended in TBS (140 mM NaCl, 50 mM Tris-HCl, pH 7.4) to a final density of $10^{10}$ bacteria per ml. Quantification was done by plating bacteria dilutions on agar. Binding of rsCD6 to bacteria was studied following a method described previously (cf. M. R. Sarrias et al., *J. Biol. Chem.* 2005, vol. 280, pp. 35391-8).

Purification of Soluble Cd6 from Human Serum

One liter of human plasma pooled from healthy blood donors was obtained from the Blood Bank of the Hospital Clinic de Barcelona. The plasma was centrifuged at 10,000 g for 15 min and filtered through a 0.22 μm filter (Millipore, Billerica, Mass., USA). The plasma was then precipitated with 20% (w/v) $(NH_4)_2SO_4$ at 4° C. for 30 min in the presence of 2 mg/ml aprotinin and leupeptin, 1 mM PMSF, 0.02% sodium azide and 0.5% NP-40, and then centrifuged at 10,000 g for 30 min at 4° C. The resulting supernatant was brought to 70% (w/v) $(NH_4)_2SO_4$ at 4° C. for 30 min, and then centrifuged at 10,000 g for 30 min at 4° C. The pellet was resuspended in PBS and subjected to dialysis at 4° C. against PBS supplemented with 1 mM PMSF, and 0.02% sodium azide. The dialyzed protein was affinity-purified over a CNBr-activated Sepharose-4B column (Amersham Pharmacia Biotech) adsorbed with the anti-CD6 mAb SPV-L14.2. Presence of nsCD6 in the eluted fractions was assessed by sandwich ELISA with specific mAbs (cf. M. Ramos-Casals et al., "High circulating levels of soluble scavenger receptors (sCD5 and sCD6) in patients with primary Sjogren's syndrome" *Rheumatology* 2001, vol. 40, pp. 1056-9) and Western-blot. Purity was assessed by SDS-PAGE and Coomassie blue staining.

LPS-binding ELISA Assays

Twelve μg of LPS purified from *E. coli* O55:B5, O111:B4, or O26:B6 (Sigma) was used to coat 96-well microtiter plates (Nunc, Roskilde, Denmark) in PBS, overnight at 4° C. Non-specific binding to the wells was prevented by the addition of PBS containing 1% BSA for 1 h at room temperature. Several concentrations of biotin-labeled BSA, rsCD6 or nsCD6 were then added to the wells and incubated for 1 h at RT. Bound protein was detected by the addition of a 1:1000 dilution of HRP-labeled streptavidin (DAKO, Glostrup, Denmark), incubating for 30 min at RT. Between each incubation step, unbound protein or HRP-streptavidin was washed off three times with PBS plus 0.01% Tween-20. Color was developed by adding 3,3',5,5'-tetramethylbenzidine liquid substrate (Sigma), and the absorbance was read at 405 nm. The assay was repeated three times with similar results.

Binding Assays of Soluble Proteins to FITC-Re-LPS

A fluorescent Re-LPS derivative (FITC-Re-LPS) was prepared in which the phosphoethanolamine group of Re-LPS was bound to FITC and prepared by a previously described method (cf. R. R. Skelly et al., "Stimulation of T-independent antibody responses by hapten-lipopolysaccharides without repeating polymeric structure", *Infect. Immun.* 1979, vol. 23, pp. 287-93). Fluorescence measurements were carried out using an SLM-Aminco AB-2 spectrofluorimeter with a thermostated cuvette holder (±0.1° C.), using 5×5 mm pathlength quartz cuvettes. Fluorescence emission spectra of FITC-Re-LPS (0.5 μg/ml) were measured in the presence and absence of either rsCD6 or rsCD5 in 100 mM NaCl, 2 mM EDTA, 5 mM Tris-HCl buffer (pH 8) at 15° C. The blanks (protein alone) and FITC-Re-LPS samples (with and without protein) were excited at 470 nm and emission spectra recorded from 500 to 650 nm. The apparent Kd for FITC-Re-LPS/protein complexes was obtained by analyzing the time dependence of the fluorescence change when 0.5 µg/ml FITC-Re-LPS reacted with various concentrations of either rsCD6 or rsCD5 at 15° C. Fluorescence emission was monitored at 520 nm for 30 min. These experiments were performed twice and in duplicates, as previously described for Kd determination of the Re-LPS interaction with LBP, CD14, surfactant protein A, and rSpα (cf. M. R. Sarrias et al., *J. Biol. Chem.* 2005, vol. 280, pp. 35391-8; P. S. Tobias et al., "Lipopolysaccharide binding protein-mediated complexation of lipopolysaccharide with soluble CD14", *J. Biol. Chem.* 1995, vol. 270, pp. 10482-8; and I. Garcia-Verdugo et al., "Interaction of SP-A (surfactant protein A) with bacterial rough lipopolysaccharide (Re-LPS), and effects of SP-A on the binding of Re-LPS to CD14 and LPS-binding protein", *Biochemical Journal* 2005, vol. 391, pp. 115-24).

Fluorescence emission anisotropy measurements were obtained with Glan Prism polarizers as previously described (cf. I. Garcia-Verdugo et al., *Biochemical Journal* 2005, vol. 391, pp. 115-24). Excitation and emission wavelengths were set at 470 and 520 nm, respectively.

Bacteria and LPS Aggregation Assays

The bacteria aggregation assays were performed as previously described (cf. M. R. Sarrias et al., *J. Biol. Chem.* 2005, vol. 280, pp. 35391-8). LPS aggregation induced by rsCD6 was studied at 15° C. by measuring the change in absorbance at 400 nm in a Beckman DU-640 spectrophotometer as described (cf. I. Garcia-Verdugo et al., *Biochemical Journal* 2005, vol. 391, pp. 115-24). Briefly, the sample and reference cuvettes were first filled with Re-LPS (100 µg/ml, final concentration) in 5 mM Tris-HCl buffer (pH 7.4), 150 mM NaCl, 0.2 mM EDTA. After a 10 min equilibration period at 15° C., rsCD6 was added to the sample cuvette at the indicated concentration, and the change in absorbance at 400 nm was monitored. Next, $Ca^{2+}$ (2.5 mM) was added to both the sample and reference cuvettes, and the change in absorbance was monitored again. $Ca^{2+}$-dependent LPS aggregation was reversed by adding EDTA (5 mM, final concentration).

Flow Cytometry Assays

Cell-binding properties of soluble proteins were assessed as previously described (cf. J. Calvo et al., "Identification of a natural soluble form of human CD5" *Tissue Antigens* 1999, vol. 54, pp. 128-37). Binding of LPS to cell surface CD6 was assessed by using the 2G5-CD6.wt cell line. Briefly, $2 \times 10^5$ cells were incubated with different amounts of LPS-FITC from *E. coli* O111:B4 (Sigma) in the presence of blocking buffer (PBS plus 10% human AB serum, 2% FCS and 0.02% sodium azide). After 1 h of incubation at 4° C., the cells were washed twice with washing buffer (PBS plus 2% FCS and 0.02% sodium azide). For competition studies, 15 µg of FITC-LPS were incubated for 30 min on ice with 2×105 2G5-CD6.wt cells in the presence of different amounts of rsCD5 or rsCD6.

CD6 Immunoprecipitation

For immunoprecipitation of cell surface bound CD6 (mCD6), $1 \times 10^6$ HUT-78 T cells were surface labeled with EZ-Link PEO-maleimide-activated biotin (Pierce, Perbio Science, Cheshire, UK) following the manufacturer's instructions. Then, membranes were solubilized with Triton X-100 detergent and proteins immunoprecipitated for 2 h at 4° C. with 1 µg of anti-CD6 mAb (161.8) plus 20 µl of 50% Protein A Sepharose CL-4B beads (Amersham Biosciences). Immune complexes were analyzed by Western Blotting as described (cf. I. Gimferrer et al., *J. Biol. Chem.* 2003, vol. 278, pp. 8564-71).

LPS-induced Endotoxic Shock

C57BL/6J mice (8-weeks old) were injected i.p. with a lethal dose of LPS from *E. coli* O111:B4 (Sigma, St. Louis, Mo.) (30 mg/kg) in a volume of 250 µl sterile saline solution. Administration of 25 µg of either rsCD5 (10 mice) or rsCD6 (16 mice) was carried out 1 h prior to the LPS challenge. Control mice received the same volume of sterile saline solution (26 mice). The percentage of survival mice was analyzed using Gradpath prism 4.0 and the log-rank t-test P-values were calculated.

The experimental procedure was approved by the ethics committee of the University of Murcia and performed in accordance with institutional animal care guidelines that comply with regulations in Spain (RD 1201/2005), Europe (86/609) and the National Institutes of Health's Guide for the Care and Use of Laboratory Animals.

Determination of Cytokine Serum Levels

The systemic release of TNF-α, IL-1β and IL-6 cytokines was determined in pooled serum samples from 6 mice of each group by ELISA according to manufacturer's instructions (R&D Systems, Minneapolis, Minn.). Data are expressed as mean±SEM. Statistical differences in the results were evaluated by the two-tailed Student's t test.

EXAMPLE 1 rsCD6 Binds to Gram-positive and Gram-negative Bacteria

To determine whether the ectodomain of human CD6 could directly bind to the surface of whole bacteria, the approach described in D. W. Dunne et al., "The Type-I Macrophage Scavenger Receptor Binds to Gram-Positive Bacteria and Recognizes Lipoteichoic Acid", *Proceedings of the National Academy of Sciences of the United States of America* 1994, vol. 91, pp. 1863-7 was used. Thus, biotin-labeled recombinant soluble proteins encompassing the ectodomains of human CD5, CD6 and Spα (rsCD5, rsCD6, and rSpα) (FIG. 1A) were incubated with bacterial suspensions and their binding to bacterial pellets further assayed by SDS-PAGE and western blotting against streptavidin-HRP. The results show that rsCD6 bound to Gram-positive and -negative bacteria (FIG. 1B), indicating that this protein possesses bacterial binding activity. In contrast, neither rsCD5 nor the negative control BSA bound to bacterial suspensions. As illustrated by FIG. 1C, the presence of biotin-labeled rsCD6 was greatly reduced in *E. coli* and *S. aureus* bacterial cell pellets in the presence of EDTA. This indicates that rsCD6 mediates $Ca^{2+}$-dependent recognition of cell wall components from Gram-positive and -negative bacteria.

To determine whether the observed binding of rsCD6 to bacteria was specific and to identify which bacterial cell surface structures were being recognized, competition experiments were designed in which biotin-labeled rsCD6 was incubated with increasing concentrations of purified LPS, or LTA, before the addition of a suspension of either *E. coli* or *S. aureus* ($5 \times 10^7$ cells). LPS and LTA were assayed because they are ubiquitous cell surface components of these microorganisms. As illustrated by FIG. 1D, binding of biotin-labeled rsCD6 to *E. coli* was competed in a dose-dependent manner by LPS (from *E. coli*), but not by LTA (from *S. aureus*). On the contrary, when the binding of rsCD6 to *S. aureus* was studied, LPS did not affect such interaction. Interestingly, this binding was competed in a dose-dependent manner by LTA from *S. aureus*.

EXAMPLE 2

Purification of nsCD6 from Human Serum

Figure 2:
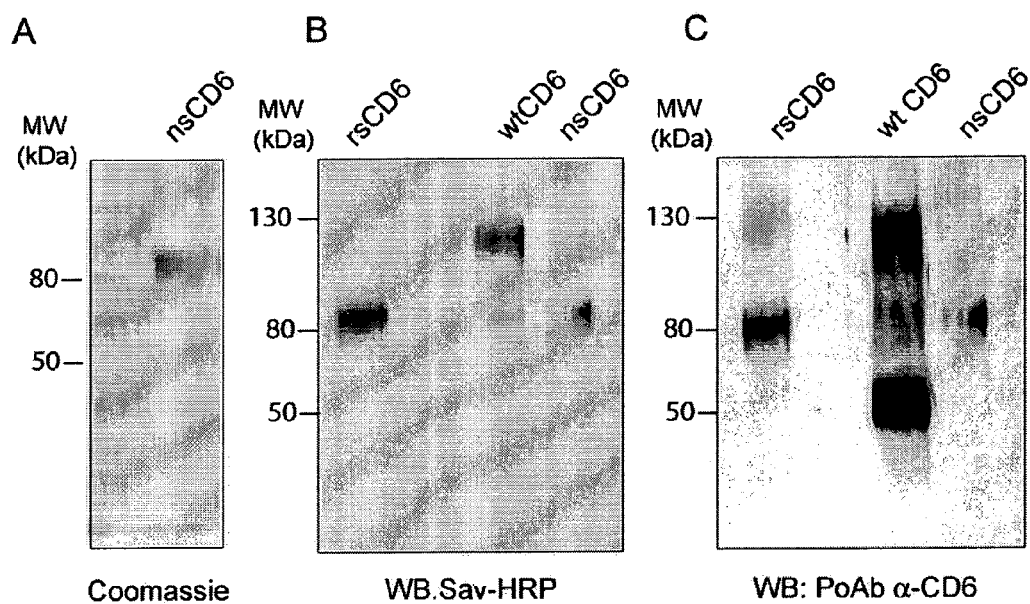
FIG. 2 shows characterization of affinity-purified circulating CD6 from human serum. A) Coomassie blue staining of affinity-purified nsCD6 from human serum. B) Western blot analysis of biotin-labeled purified nsCD6 and rsCD6 proteins and membrane CD6 immunoprecipitated from surface biotinylated HUT-78 T cells with streptavidin-HRP. C) Western blot analysis of the same biotin-labeled proteins as in B) with a rabbit polyclonal antiserum specific for the extracellular region of CD6. D) Flow cytometry analysis of the reactivity of biotin-labeled rsCD5, rsCD6, nsCD6 or BSA with the K652 and Raji cells. Bound protein was detected with streptavidin-Tricolor. F.I. means "fluorescence intensity" and C.N. means "cell number".
Figure 2:
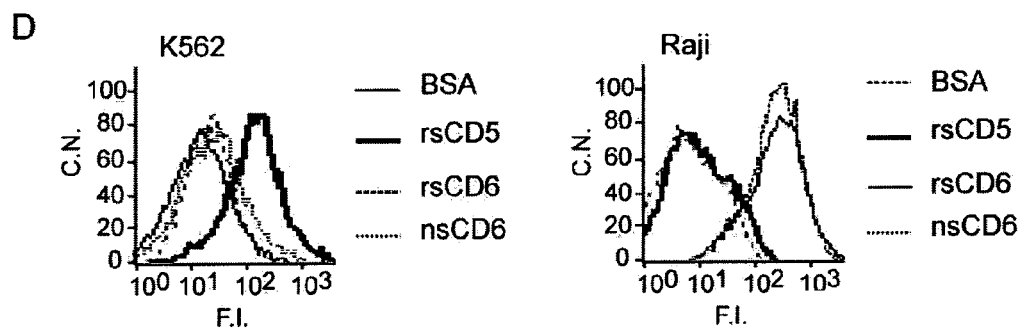

Natural sCD6 was affinity-purified from 1 l of pooled plasma. This yielded 6 μg of a single protein with a molecular weight (MW) of 80 kDa as deduced from SDS-PAGE analysis and Coomassie blue staining (FIG. 2A). The observed MW closely resembles that of recombinant soluble CD6 (rsCD6) produced in the laboratory, which is exclusively composed of the three extracellular SRCR domains of CD6, and is in contrast to that of the membrane form of CD6 (mCD6), which ranges from 105 to 130 kDa, depending on its degree of phosphorylation. The observed MW of the three different CD6 forms, i.e. rsCD6, nsCD6 and mCD6 immunoprecipitated from human HUT-78 T cells is shown in FIG. 2B. The purified nsCD6 protein was identified as CD6 by Western blotting assays with a polyclonal antiserum raised against the extracellular region of human CD6 (FIG. 2C). In cell binding experiments, both biotin-labeled rsCD6 and nsCD6 bound to Raji B cells but not to K562 erythroleukemic cells, in accordance with the differential expression of the CD6 ligand (ALCAM/CD166) (FIG. 2D).

EXAMPLE 3

Binding of rsCD6 to LPS and Kinetics of the rsCD6-LPS Interaction

Figure 3:
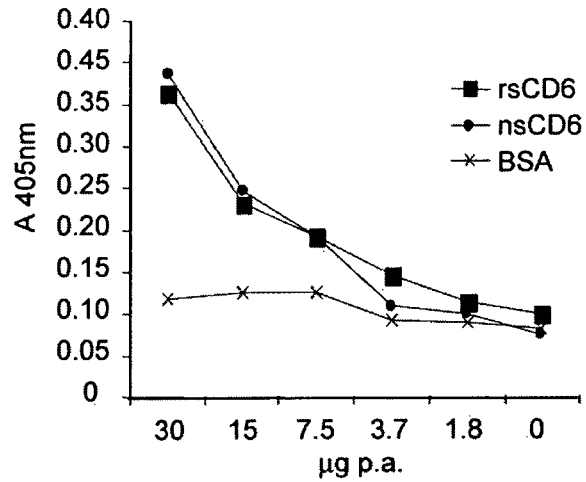
FIG. 3 refers to the binding of rsCD6 to LPS. A) ELISA showing direct binding of affinity-purified nsCD6 and rsCD6 to LPS. LPS purified from *E. coli* was coated into 96-well microtiter plates. Several concentrations of biotin-labeled rsCD6, nsCD6 or BSA, were then added to the wells, and bound protein was detected with streptavidin-HRP. Binding of rsCD6 or rsCD5 to Re-LPS was then monitored by changes in FITC-Re-LPS fluorescent properties. P.a. means "protein added". B) rsCD6, but not rsCD5, induces a significant increase in fluorescence anisotropy (referred as "A") upon binding to FITC-Re-LPS, which increases with increasing rsCD6 concentration. C) Net change in fluorescence emission intensity (referred as "F") of FITC-Re-LPS at 520 nm upon addition of increasing amounts of rsCD6 or rsCD5. The apparent Kd for FITC-Re-LPS/sCD6 complexes, calculated from the saturation curve fitted to a rectangular hyperbola, was $2.69\pm0.32\times10^{-8}$ M.
Figure 3:
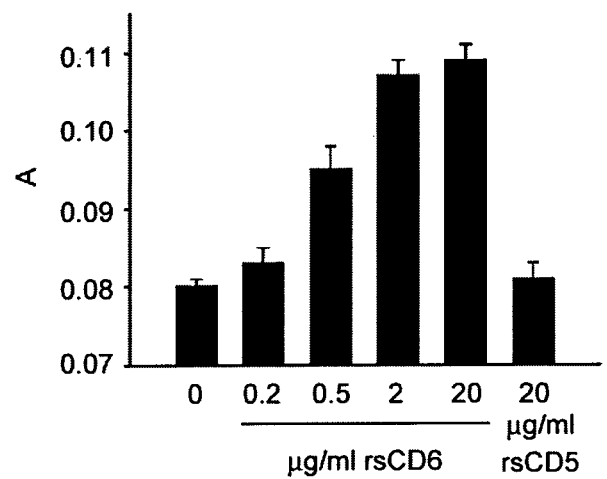
Figure 3:
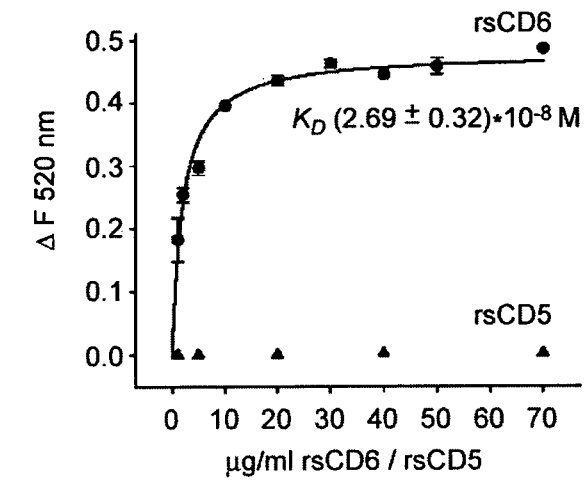

Further confirmation of the rsCD6-LPS interaction was obtained from direct binding ELISA assays in which plates were coated with LPS purified from three different *E. coli* strains (O55:B5, O111:B4, or O26:B6), and assayed for binding of biotin-labeled rsCD6, nsCD6, or BSA. The results presented in FIG. 3A show that, in accordance with the bacterial binding experiments in FIG. 1, both natural and recombinant soluble CD6 forms bound to LPS in a dose-dependent fashion. No BSA-LPS interaction could be observed.

The binding of rsCD6 and rsCD5 to a rough mutant (Re595) of LPS (Re-LPS) in solution was studied next by analyzing the changes in fluorescent properties of FITC-Re-LPS such as anisotropy and intensity. FIG. 3B shows the binding of rsCD6 and rsCD5 to FITC-Re-LPS by measuring fluorescence anisotropy of the labeled LPS molecule. Fluorescence anisotropy measurements depend on the rate and extent of the rotational motion of the fluorophore during the lifetime of the excited state. Addition of different amounts of rsCD6 to FITC-Re-LPS caused a protein concentration-dependent increase of the anisotropy values of FITC-Re-LPS, indicating that the binding of rsCD6 to Re-LPS caused mechanical restrictions of the rotational mobility of the dye. Control experiments were done with free fluorescein to demonstrate that all of these changes did not result from the interaction of rsCD6 with the dye (fluorescein), but with the LPS molecule (data not shown). The fluorescence emission anisotropy of free fluorescein was very low and was not affected by addition of 3-fold excess of rsCD6 (data not shown). On the other hand, rsCD5 did not cause any change in FITC-Re-LPS fluorescence anisotropy, indicating that this protein does not bind to Re-LPS.

Addition of rsCD6, but not rsCD5, to FITC-Re-LPS in solution also produced an increase of total fluorescence emission intensity of fluorescent LPS. The time dependence of the change in fluorescence emission intensity at 520 nm when FITC-Re-LPS reacted with increasing amounts of either rsCD6 or rsCD5 was determined. FIG. 3C shows that the magnitude of the fluorescence intensity change increased as a function of rsCD6 concentration, but not rsCD5 concentration, and was saturable. These results allowed to determine the affinity of rsCD6 binding to LPS. The apparent Kd for FITC-Re-LPS/rsCD6 complexes, calculated from the saturation curve fitted to a rectangular hyperbola, was 2.69 (±0.32) $10^{-8}$ M.

EXAMPLE 4

Binding of LPS to Cell-surface CD6

Figure 4:
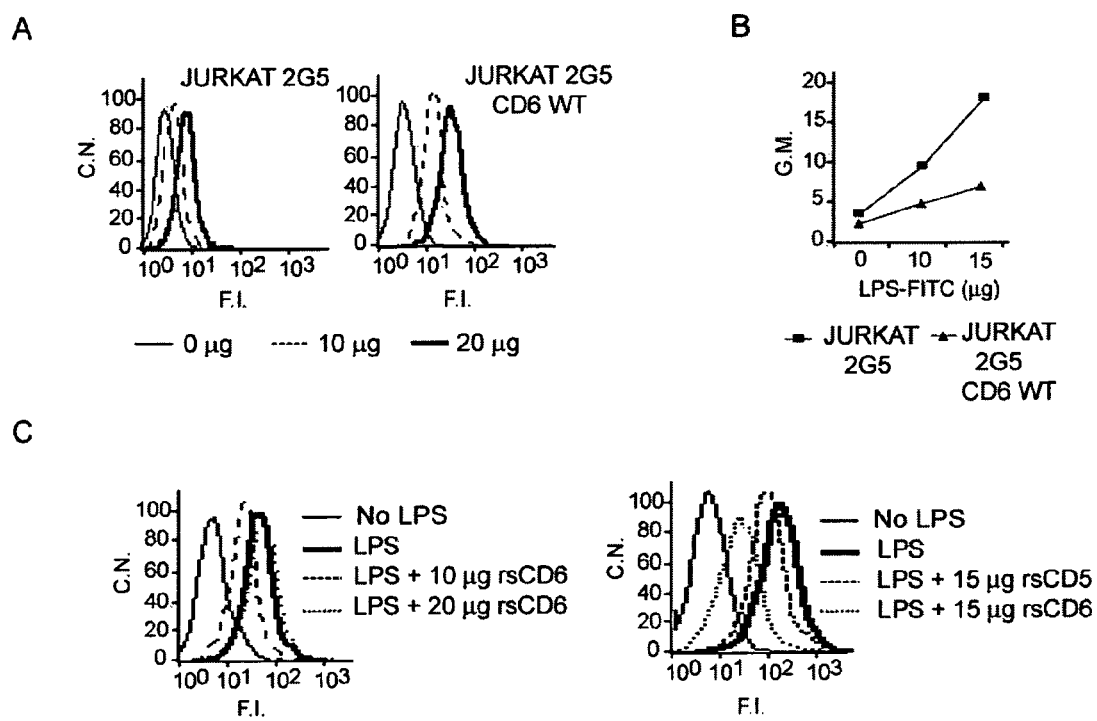
FIG. 4 shows the binding of LPS from *E. coli* to cell surface CD6. A) Flow cytometry analysis showing direct binding of increasing amounts of LPS-FITC (0, 10, 20 μg) to parental and CD6.wt-transfected 2G5 cells. C.N. means "cell number" and F.I. "fluorescence intensity". B) To ease comparison, mean fluorescence intensities of A) were plotted against the amount of LPS-FITC added to each cell line. G.M. means "Geo mean". C) Competition studies of LPS-FITC binding to the 2G5-CD6.wt transfectants. Cells were incubated with 15 μg of FITC-LPS in the presence of increasing amounts (0, 10, 20 μg) of rsCD6 (left) or with 15 μg of either rsCD6 or rsCD5 (right). Fluorescence intensity was analyzed by flow cytometry.

To determine whether the LPS-CD6 interaction occurs as well with the receptor expressed on the cell surface, studies were performed by staining with FITC-labeled LPS of 2G5 cells, a Jurkat cell derivative selected for deficient CD5 and CD6 expression. As shown by the flow cytometry studies displayed in FIGS. 4A and 4B, fluorescence intensity was higher in 2G5 cells stably expressing wild-type CD6 (2G5-CD6.wt) compared to parental untransfected 2G5 cells. Further confirmation of these results was obtained from competition binding experiments. 2G5-CD6.wt cells were stained with a single amount of FITC-LPS in the presence of increasing amounts of rsCD6. In these experiments, binding of FITC-LPS to 2G5-CD6.wt cells was inhibited in a dose-dependent manner by rsCD6, but not with rsCD5, used as a negative control (FIG. 4C), indicating that the inhibition was specific. From these data it is concluded that LPS is able to interact with CD6 on the cell surface.

EXAMPLE 5

Binding of rsCD6 Leads to Both Bacteria and LPS Aggregation

FIG. 5A shows that presence of rsCD6 induced aggregation of Gram-negative (*E. coli*) as well as Gram-positive (*S. aureus*) bacteria. In accordance with its inability to bind bacteria, rsCD5 was also unable to induce their aggregation, as it did not the negative control HSA.

Since binding of rsCD6 to whole Gram-negative bacteria was enhanced by the presence of $Ca^{2+}$ in the binding buffer (see FIG. 1) it was further explored the process of Re-LPS aggregation induced by rsCD6 in the presence of $Ca^{2+}$. This was analyzed by measuring changes in light absorbance at 400 nm (FIG. 5B). These experiments were carried out under the same ionic conditions as binding studies with fluorescent LPS, except that $Ca^{2+}$ as well as concentrations of Re-LPS, 200 times higher were needed to produce detectable light absorption at 400 nm. FIG. 5B shows that LPS molecules were able to aggregate in buffers containing $Ca^{2+}$ and that low concentrations of rsCD6 induced a further aggregation of LPS. Together, these data suggest that, in the presence of $Ca^{2+}$, rsCD6 may contribute to increase the size of bacterial as well as of LPS aggregates.

EXAMPLE 6 rsCD6 Prevents LPS-induced Septic Shock in Mice

Figure 5:
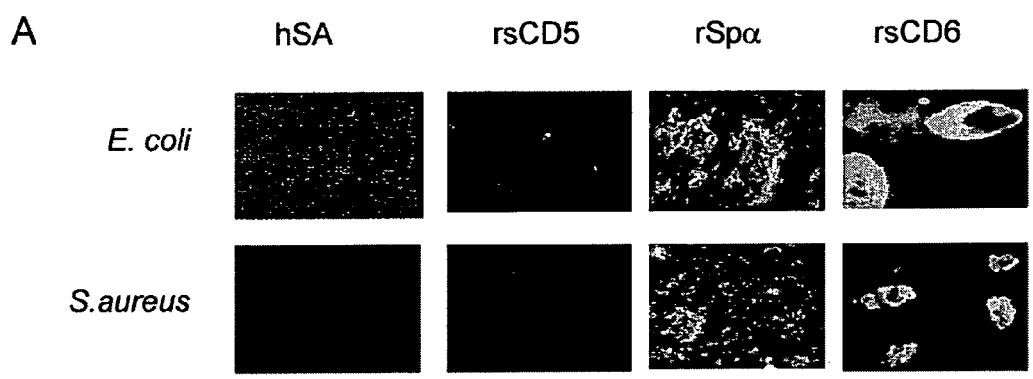
FIG. 5 shows that rsCD6 induces bacterial aggregation. A) FITC-labeled *E. coli* and *S. aureus* bacterial suspensions were incubated overnight at room temperature (RT) with rsCD6 or rsCD5 (2 μM) in the presence of 5 mM $Ca^{2+}$. Equimolar concentrations of rSpα and HSA were used as positive and negative control, respectively. Aggregation was observed by direct examination on a fluorescence microscope. B) Kinetics of $Ca^{2+}$-dependent Re-LPS aggregation in the absence (●) and presence of increasing concentration of rsCD6. The final concentrations of Re-LPS, calcium, and EDTA were 100 μg/mL, 2.5 mM and 5 mM, respectively. The final concentrations of rsCD6 were 0.25 (○), 0.50 (Δ), 1.0 (●), 2.0 (□) μg/ml. One representative experiment of two performed is shown. Time is indicated as T (min).
Figure 5:
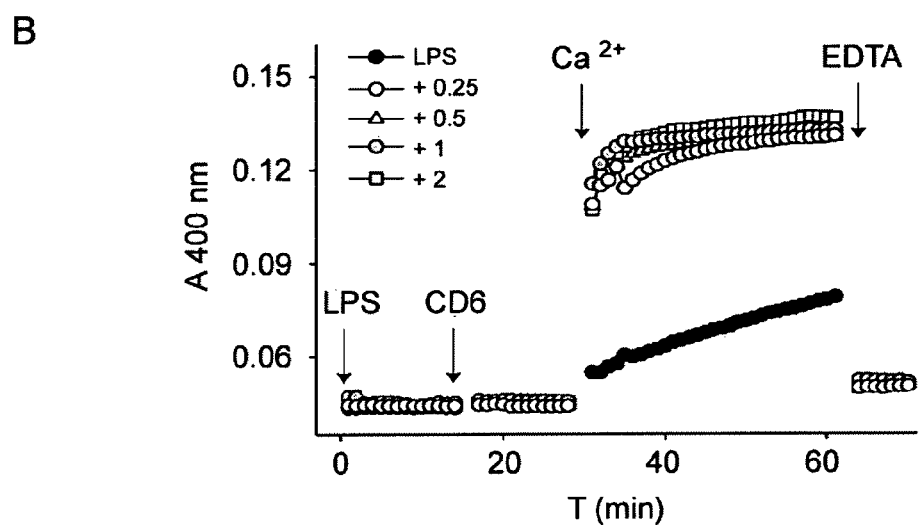
Figure 6:
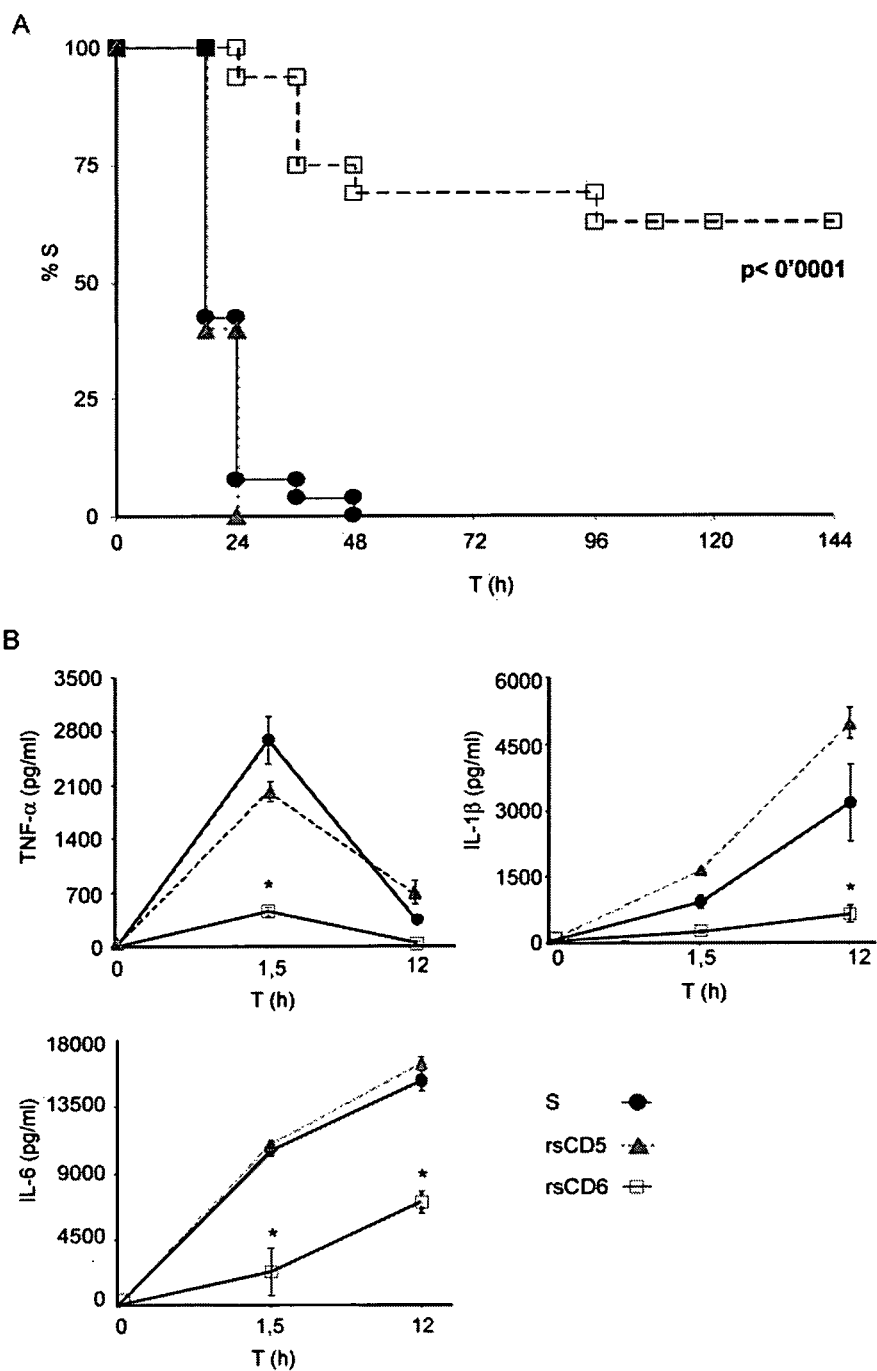
FIG. 6 shows the effect of rsCD6 and rsCD5 on survival rate and cytokine serum levels following LPS-induced septic shock. A) Survival (S) graph. C57BL/6J mice (8-weeks old) were injected i.p. with a lethal dose of LPS from *E. coli* O111:B4 (30 mg/kg) 1 h after i.p. administration of either sterile saline solution (referred as "S") (n=26) or rsCD5 (n=10) or rsCD6 (n=16) (25 μg, each). The percentage of survival mice was analyzed using Gradpath prism 4.0 and the log-rank t-test P-values were calculated. B) Circulating levels of cytokines in LPS-challenged mice. Plasma levels of TNF-α, IL-1β and IL-6 were quantified by ELISA at different times after LPS injection. Data are expressed as mean±SEM. Statistical differences in the results were evaluated by the two-tailed Student's t test. *, Statistically significant difference ($P<0.05$). Time is indicated as T (min).

The data on FIG. 5 lead to the notion that circulating CD6 (nsCD6) may contribute to the clearance of LPS particles, reducing their inflammatory effect. Increasing the amount of circulating rsCD6 might therefore have a protective effect in situations in which an excess of LPS could be lethal. To test this, it was assessed whether administration of the rsCD6 into mice would improve their survival in front of LPS-induced septic shock. As observed in FIG. 6A, administration of a single i.p. dose of 25 μg of rsCD6, but not rsCD5 in mice one hour prior to i.p. LPS challenge significantly enhanced their survival rate as compared with the saline control (up to 70%). In accordance with this data, administration of rsCD6 induced a significant reduction on the levels of plasma pro-inflammatory cytokines TNF-α, IL-1β and IL-6 in these mice (FIG. 6B).

EXAMPLE 7 rsCD6 Binds to Zymosan Extracted from Yeast (*Saccharomices cerevisae*)

Twelve μg of LPS purified from *E. coli* O111:B4 (Sigma), Zymosan from *Saccharomyces cerevisae* (Sigma), peptidoglycan purified from *S. aureus* (Fluka) or Bovine Serum Albumin (BSA), were used to coat 96-well microtiter plates (Nunc, Roskilde, Denmark) in PBS, overnight at 4° C. Non-specific binding to the wells was prevented by the addition of PBS containing 1% BSA for 1 h at room temperature. Several concentrations of rsCD6 were then added to the wells and incubated for 3 h at room temperature. Bound protein was detected by the addition of a 1:200 dilution of biotin-labeled mAb anti-CD6 (MAE) for 1 h at RT, followed by a 1:1000 dilution of HRP-labeled streptavidin (DAKO, Glostrup, Denmark), which was incubated for 30 min at RT. Between each incubation step, unbound protein or HRP-streptavidin was washed off three times with PBS plus 0.01% Tween-20. Color was developed by adding 3,3',5,5'-tetramethylbenzidine liquid substrate (Sigma), and the absorbance was read at 450 nm. The assay was repeated three times with similar results.

Figure 7:
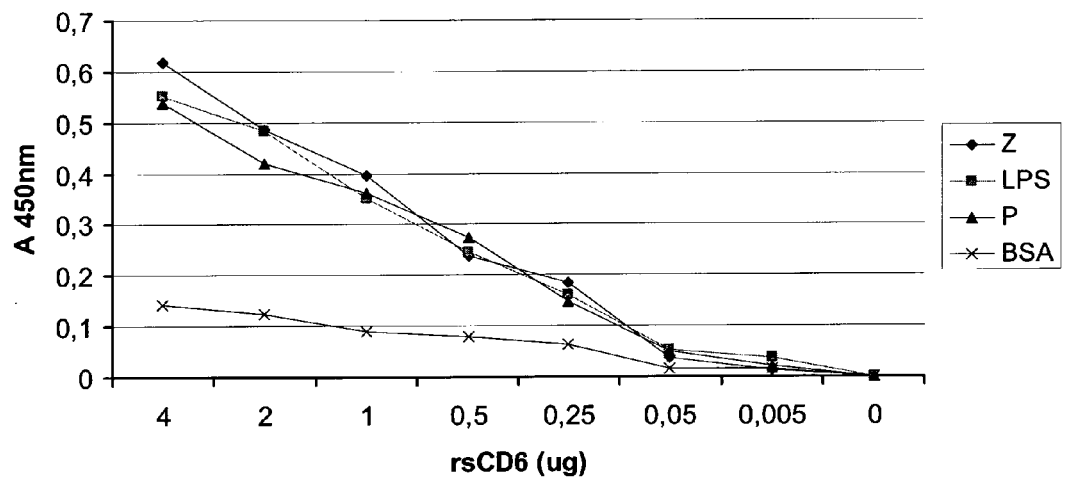
FIG. 7 shows the binding of rsCD6 to zymosan extracted from yeast (*Saccharomices cerevisae*). Results of ELISA assay where A means "Absorbance", Z "Zymosan", and P "peptidoglycan" purified from *S. aureus*. LPS purified from *E. coli* strain O111:B4 and BSA are the positive and negative controls.

The results presented in FIG. 7 show that rsCD6 bound to zymosan, peptidoglycan and LPS in a dose-dependent fashion. No BSA-rsCD6 interaction could be observed. This ELISA experiment indicates that peptidoglycan, a highly abundant structure from the surface of Gram-positive bacteria, is also recognized by rsCD6. Interestingly, rsCD6 is also able to bind to yeast zymosan.

EXAMPLE 8 rsCD6 Binds to Human Cytomegalovirus Particles

One microgram of a polyclonal anti-CMV antibody (BiosPacific, Emeryville, Calif., USA) was used to coat 96-well microtiter plates (Nunc, Roskilde, Denmark) in PBS, overnight at 4° C. Non-specific binding to the wells was prevented by the addition of PBS containing 3% BSA for 1 h at RT. One microgram of a suspension of CMV particles (ABI Advanced Biotechnologies, Maryland, USA) then added to the wells and incubated for 1 h at RT. Then, different concentrations of rsCD6 protein were added to the wells and incubated for 3 h at RT. Bound protein was detected by the addition of a 1:200 dilution of biotin-labeled mAb anti-CD6 (MAE) for 1 h at RT, followed by a 1:1000 dilution of HRP-labeled streptavidin (DAKO, Glostrup, Denmark), which was incubated for 30 min at RT. Between each incubation step, unbound protein or HRP-streptavidin was washed off three times with PBS plus 0.01% Tween-20. Color was developed by adding 3,3',5,5'-tetramethylbenzidine liquid substrate (Sigma), and the absorbance was read at 450 nm. The assay was repeated three times with similar results.

Figure 9:
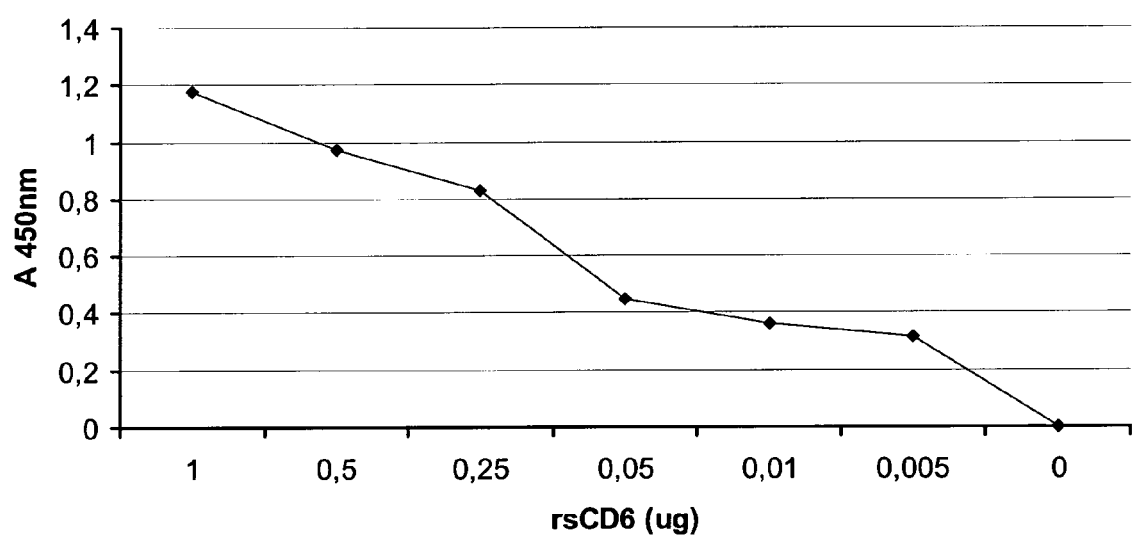
FIG. 9 shows the binding of rsCD6 binds to human cytomegalovirus particles. Results of ELISA assay.

The results presented in FIG. 9 show that rsCD6 bound to CMV particles in a dose-dependent fashion. Background non-specific binding of CD6 to antibody-coated wells was subtracted. These results suggest that rsCD6 is able to bind to the surface of human cytomegalovirus.

EXAMPLE 9 rsCD6 Binds to HIV Surface Protein gp120

100 μl of serum-free culture supernatant from cell transfectants expressing rsCD6 were used to coat 96-well microtiter plates (Nunc, Denmark), o/n at 4° C. Non-specific binding to the wells was prevented by the addition of PBS containing 3% BSA for 1 h at RT. Then, different concentrations of recombinant gp120 protein from HIV (Immunodiagnostics, through the NIH AIDS Research and Reference Reagent Program, Germantown, Md., USA) were added to the wells and incubated for 1 h at RT. Bound protein was detected by the addition of 500 ng of an anti-gp120 mAb (hm Ab 2G12, Immunodiagnostics) in 2% heat-inactivated human serum for 1 h at RT, followed by a 1:200 dilution of HRP-labeled anti-human IgG antibody (DAKO, Glostrup, Denmark), which was incubated for 30 min at RT. Between each incubation step, unbound protein or HRP-streptavidin was washed off three times with PBS plus 0.01% Tween-20. Color was developed by adding 3,3',5,5'-tetramethylbenzidine liquid substrate (Sigma), and the absorbance was read at 450 nm. The assay was repeated three times with similar results.

Figure 8:
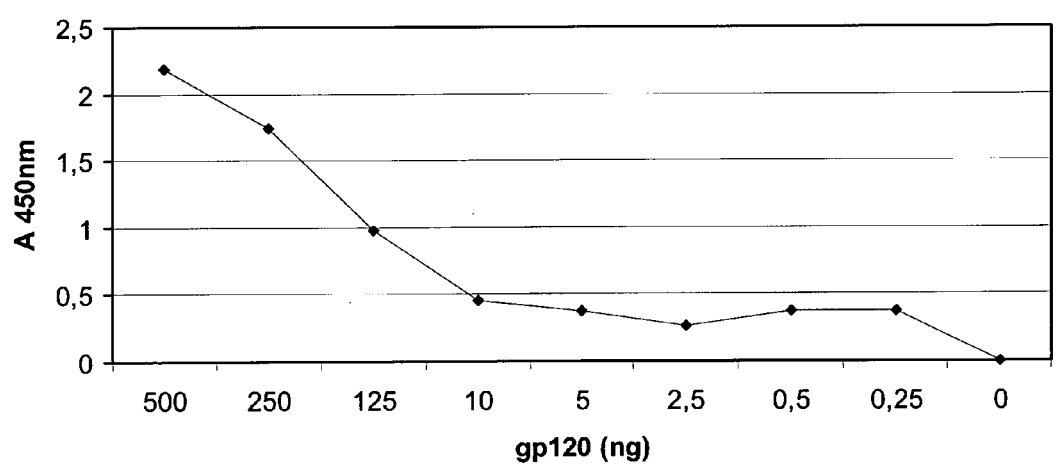
FIG. 8 shows the binding of rsCD6 binds to HIV surface protein gp120. Results of ELISA assay.

The results presented in FIG. 8 show that rgp120 bound to rsCD6 in a dose-dependent fashion. Background non-specific binding of rsgp120 to blocking buffer on the wells was subtracted. These results suggest that rsCD6 is able to bind to rgp120, the major outer protein of Human Immunodeficiency Virus.

The invention claimed is:

1. A method for therapeutic and/or preventive treatment of sepsis in a mammal caused by a Gram-positive and/or Gram-negative bacterium and/or endotoxins, comprising administering to said mammal in need thereof an effective amount of a CD6 product.

2. The method according to claim 1, wherein the sepsis is severe sepsis.

3. The method according to claim 2, wherein the severe sepsis is septic shock.

4. The method according to claim 1, wherein the CD6 product is a recombinant CD6.

5. The method according to claim 4, wherein the CD6 product is a human CD6 product.

6. The method according to claim 5, wherein the CD6 product comprises the amino acid sequence SEQ ID NO: 1.

7. The method according to claim 4, wherein the CD6 product is a murine CD6 product.

8. The method according to claim 1, wherein the mammal is a human.

9. The method according to claim 3, wherein the septic shock is endotoxin-induced septic shock.

* * * * *

SEQUENCE LISTING

```
<160> NUMBER OF SEQ ID NOS: 7

<210> SEQ ID NO 1
<211> LENGTH: 360
<212> TYPE: PRT
<213> ORGANISM: Homo sapiens (fragment)

<400> SEQUENCE: 1

Asp Gln Leu Asn Thr Ser Ser Ala Glu Ser Glu Leu Trp Glu Pro Gly
1               5                   10                  15

Glu Arg Leu Pro Val Arg Leu Thr Asn Gly Ser Ser Ser Cys Ser Gly
            20                  25                  30
```

Thr Val Glu Val Arg Leu Glu Ala Ser Trp Glu Pro Ala Cys Gly Ala
                35                  40                  45

Leu Trp Asp Ser Arg Ala Ala Glu Ala Val Cys Arg Ala Leu Gly Cys
 50                  55                  60

Gly Gly Ala Glu Ala Ala Ser Gln Leu Ala Pro Thr Pro Glu Leu
 65                  70                  75                  80

Pro Pro Pro Ala Ala Gly Asn Thr Ser Val Ala Ala Asn Ala Thr
                 85                  90                  95

Leu Ala Gly Ala Pro Ala Leu Leu Cys Ser Gly Ala Glu Trp Arg Leu
                100                 105                 110

Cys Glu Val Val Glu His Ala Cys Arg Ser Asp Gly Arg Ala Arg
                115                 120                 125

Val Thr Cys Ala Glu Asn Arg Ala Leu Arg Leu Val Asp Gly Gly Gly
                130                 135                 140

Ala Cys Ala Gly Arg Val Glu Met Leu Glu His Gly Glu Trp Gly Ser
145                 150                 155                 160

Val Cys Asp Asp Thr Trp Asp Leu Glu Asp Ala His Val Val Cys Arg
                165                 170                 175

Gln Leu Gly Cys Gly Trp Ala Val Gln Ala Leu Pro Gly Leu His Phe
                180                 185                 190

Thr Pro Gly Arg Gly Pro Ile His Arg Asp Gln Val Asn Cys Ser Gly
                195                 200                 205

Ala Glu Ala Tyr Leu Trp Asp Cys Pro Gly Leu Pro Gly Gln His Tyr
                210                 215                 220

Cys Gly His Lys Glu Asp Ala Gly Val Val Cys Ser Glu His Gln Ser
225                 230                 235                 240

Trp Arg Leu Thr Gly Gly Ala Asp Arg Cys Glu Gly Gln Val Glu Val
                245                 250                 255

His Phe Arg Gly Val Trp Asn Thr Val Cys Asp Ser Glu Trp Tyr Pro
                260                 265                 270

Ser Glu Ala Lys Val Leu Cys Gln Ser Leu Gly Cys Gly Thr Ala Val
                275                 280                 285

Glu Arg Pro Lys Gly Leu Pro His Ser Leu Ser Gly Arg Met Tyr Tyr
                290                 295                 300

Ser Cys Asn Gly Glu Glu Leu Thr Leu Ser Asn Cys Ser Trp Arg Phe
305                 310                 315                 320

Asn Asn Ser Asn Leu Cys Ser Gln Ser Leu Ala Ala Arg Val Leu Cys
                325                 330                 335

Ser Ala Ser Arg Ser Leu His Asn Leu Ser Thr Pro Glu Val Pro Ala
                340                 345                 350

Ser Val Gln Thr Val Thr Ile Glu
                355                 360

<210> SEQ ID NO 2
<211> LENGTH: 30
<212> TYPE: DNA
<213> ORGANISM: Artificial
<220> FEATURE:
<223> OTHER INFORMATION: PCR primer

<400> SEQUENCE: 2
tctcgtcgac atgtggctct tcttcgggat                                    30

<210> SEQ ID NO 3
<211> LENGTH: 24
<212> TYPE: DNA

```
-continued

<213> ORGANISM: Artificial
<220> FEATURE:
<223> OTHER INFORMATION: PCR primer

<400> SEQUENCE: 3
aacttctttg gggatggtga tggg                                          24

<210> SEQ ID NO 4
<211> LENGTH: 21
<212> TYPE: DNA
<213> ORGANISM: Artificial
<220> FEATURE:
<223> OTHER INFORMATION: PCR primer

<400> SEQUENCE: 4
gtcactatag aatcttctgt g                                             21

<210> SEQ ID NO 5
<211> LENGTH: 30
<212> TYPE: DNA
<213> ORGANISM: Artificial
<220> FEATURE:
<223> OTHER INFORMATION: PCR primer

<400> SEQUENCE: 5
aaaggatccc taggctgcgc tgatgtcatc                                    30

<210> SEQ ID NO 6
<211> LENGTH: 31
<212> TYPE: DNA
<213> ORGANISM: Artificial
<220> FEATURE:
<223> OTHER INFORMATION: PCR primer

<400> SEQUENCE: 6
cttctagatg accagctcaa caccaccagc a                                  31

<210> SEQ ID NO 7
<211> LENGTH: 33
<212> TYPE: DNA
<213> ORGANISM: Artificial
<220> FEATURE:
<223> OTHER INFORMATION: PCR primer

<400> SEQUENCE: 7
gcggatccct attctatagt gactgtctga aca                                33
```